United States Patent [19]
Klibanov et al.

[11] Patent Number: 5,807,735
[45] Date of Patent: Sep. 15, 1998

[54] SOLVENT-RESISTANT MICROORGANISMS

[75] Inventors: Alexander A. Klibanov; Kim Lewis, both of Newton; Anthony Ferrante, Medford, all of Mass.; Catherine L. Coyle, Mendham, N.J.; Gerben Zylstra, Roosevelt, N.J.; Michael S. P. Logan, Phillipsburg, N.J.; Matthew J. Grossman, Flemington, N.J.

[73] Assignee: Exxon Research and Engineering Company, Florham Park, N.J.

[21] Appl. No.: 831,400

[22] Filed: Apr. 1, 1997

Related U.S. Application Data

[63] Continuation of Ser. No. 413,134, Mar. 29, 1995, abandoned.

[51] Int. Cl.$^6$ .......................... C12N 15/70; C12N 15/53; C12N 9/04; C07H 21/04
[52] U.S. Cl. .................. 435/252.33; 435/172.3; 435/190; 435/252.3; 435/320.1; 536/23.1; 536/23.2; 536/23.7
[58] Field of Search ........................ 536/23.1; 435/320.1, 435/252.33, 252.3, 243

*Primary Examiner*—John L. LeGuyader
*Assistant Examiner*—Andrew Wang
*Attorney, Agent, or Firm*—Ronald D. Hantman

[57] ABSTRACT

The present invention includes microorganisms that are resistant to non-aqueous solvents. In addition, the organisms of interest are able to grow and/or carry out various organic (e.g. hydrocarbon) transformations in non-aqueous/aqueous mixtures.

The invention also includes a gene which encodes an enzyme, hydroperoxide reductase, which renders the host microorganism resistant to many organic solvents. The invention also includes the operon which includes the mutant gene and the ahpF gene which encodes an NAD(P)H dehydrogenase. The invention also includes a plasmid vehicle and a host microorganism containing these genes.

The invention also includes cloning the genes encoding for solvent-resistance into other organisms rendering them solvent-resistant. In addition, the genes encoding for a specific organic or hydrocarbon transformation are placed into the solvent resistant microorganism.

7 Claims, 4 Drawing Sheets

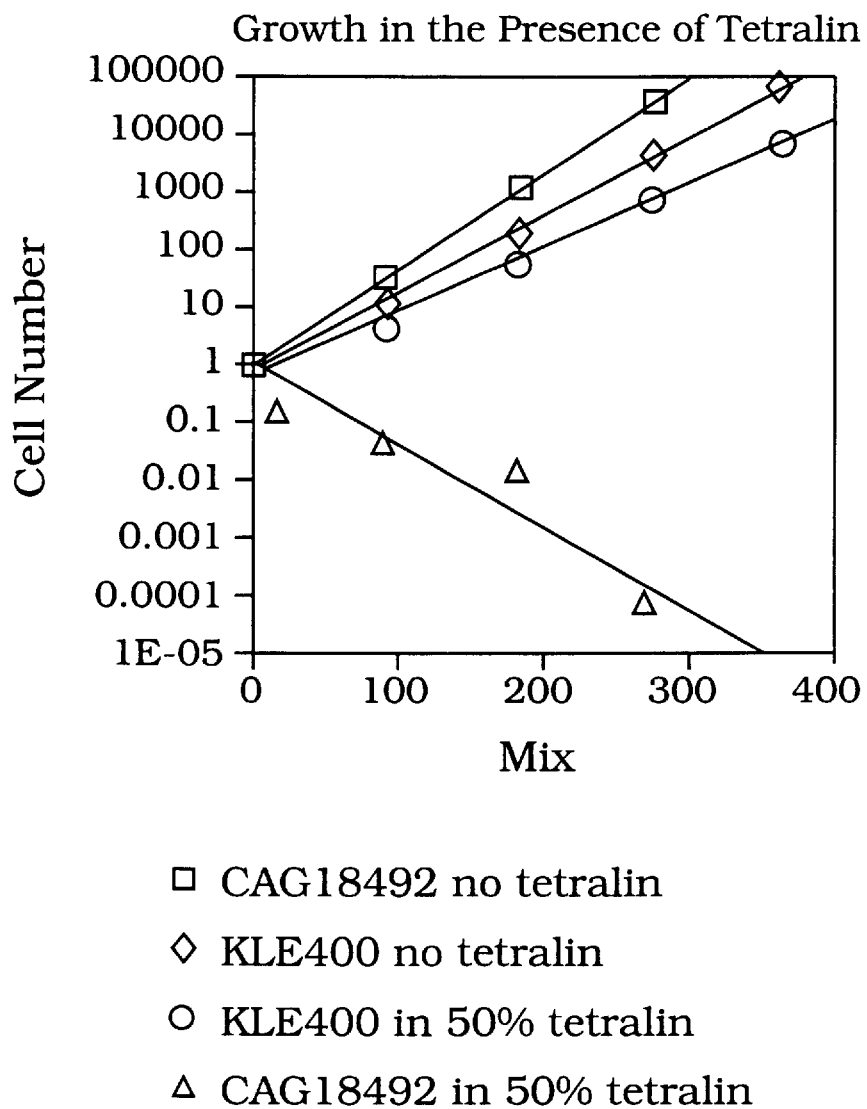
Fig. 1. Growth of resistant mutants in a tetralin emulsion.
Cell were inoculated in a 50% emulsion of tetralin in medium A and were incubated with aeration at 37C. Samples were taken at times indicated and plated for colony counting.

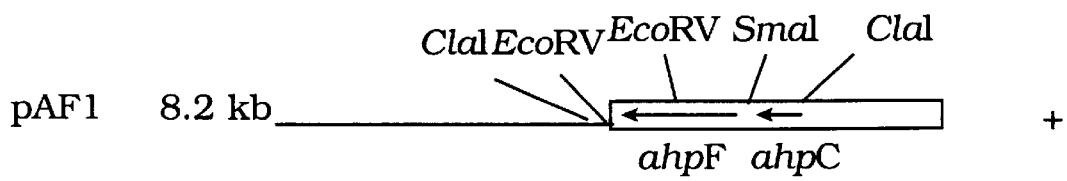
pAF1   8.2 kb — ClaI EcoRV EcoRV SmaI ClaI — ahpF ahpC   +
(The *ahpCF* operon encode alkylhdroperoxide reductase)
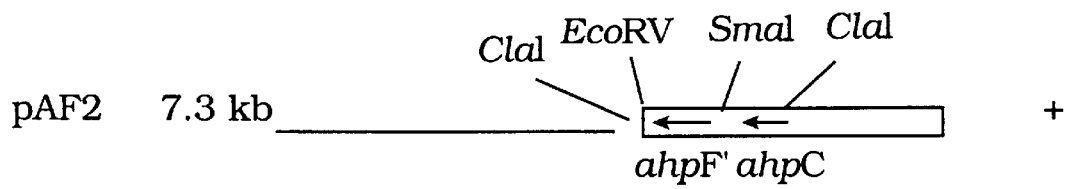
pAF2   7.3 kb — ClaI EcoRV SmaI ClaI — ahpF' ahpC   +
(Confers resistance to tetralin despite mission 2/3 of the *ahpF* gene)
pAF3   5.7 kb — ClaI —   −
Fig. 2. Deletion mapping of the tetralin resistance locus.

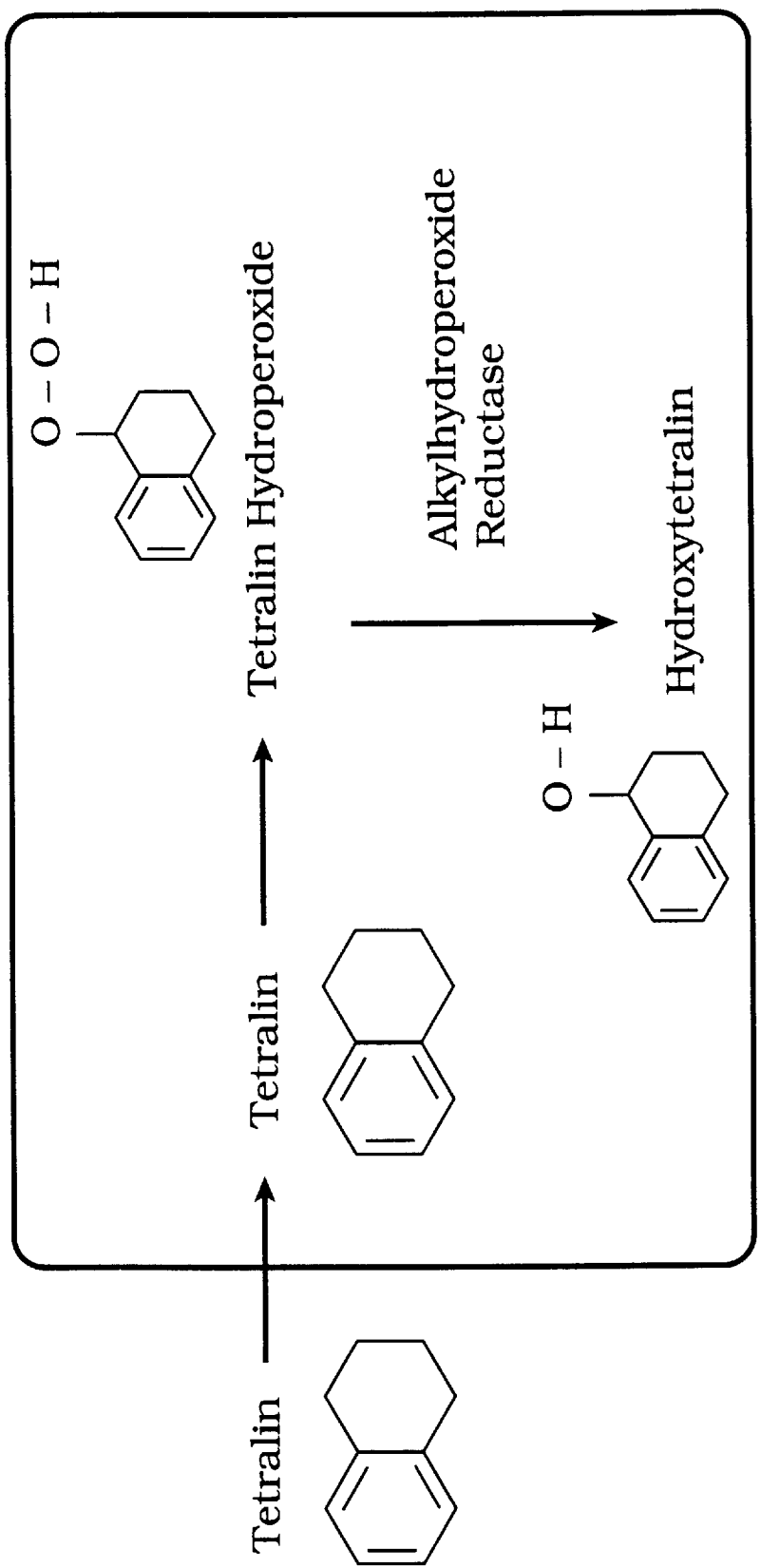
Fig. 3. A Model for Tetralin Metabolism in E. coli KLE400

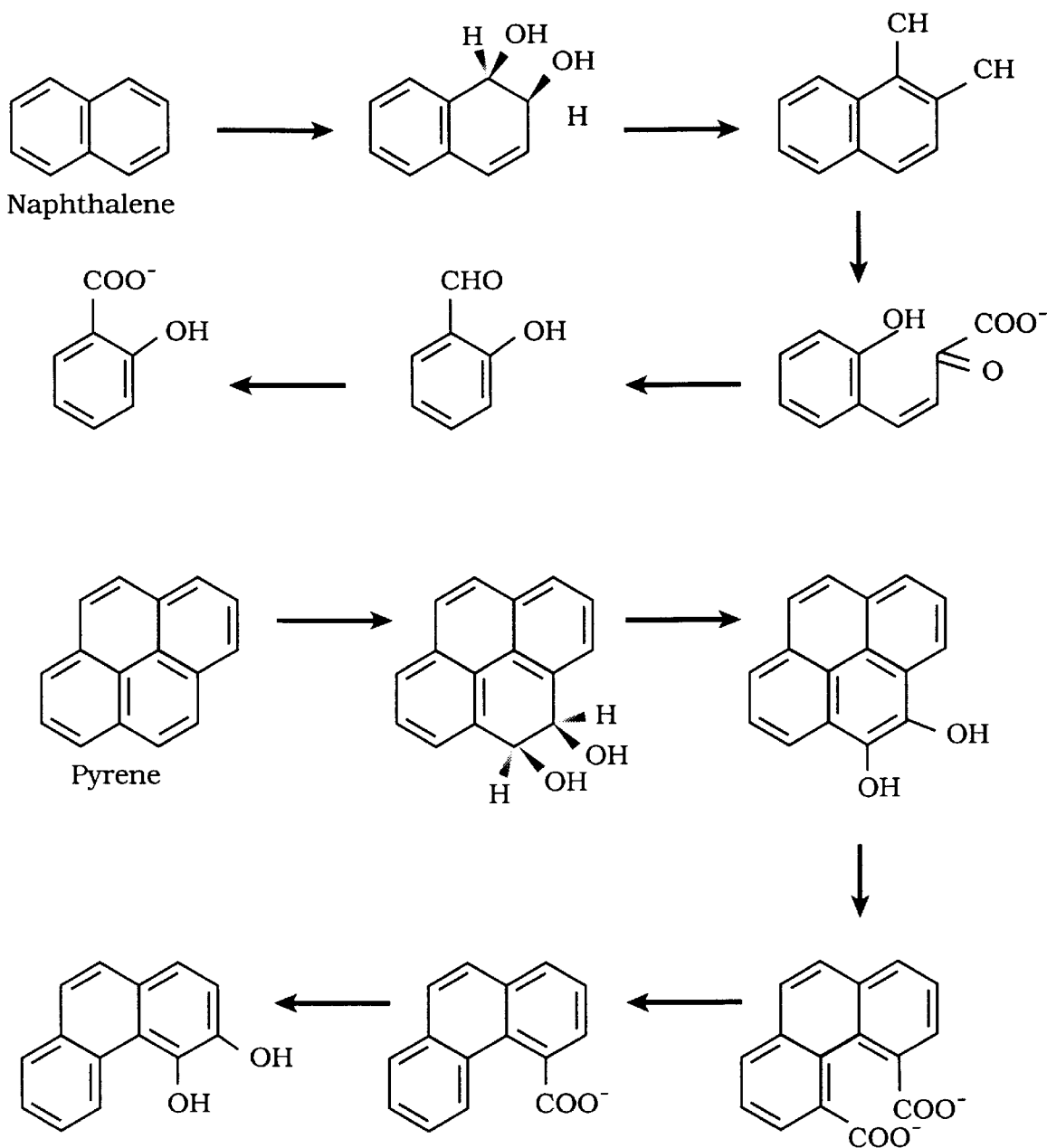
Fig. 4. Initial steps in the metabolism of naphthalene and pyrene by microorganisms.

SOLVENT-RESISTANT MICROORGANISMS

This is a continuation of application Ser. No. 08/413,134, filed Mar. 29, 1995, now abandoned.

BACKGROUND OF THE INVENTION

The present invention relates to microorganisms which are resistant to organic solvents.

Most of the work utilizing microorganisms as biocatalysts is done in aqueous solvents. Bioprocesses for the conversion and upgrading of petroleum, heavy hydrocarbon and chemical feedstocks often involve non-aqueous solvents because the substrate and/or product of the reactions are insoluble in water. Any bioprocess involving the conversion of these feeds would be aided by the development of microorganisms that are stable and active in the presence of non-aqueous solvents. This invention would provide a new series of such microorganisms that are capable of enhanced stability and activity as a result of their ability to function in non-aqueous media.

Another advantage of solvent-tolerant organisms involves the enhanced solubility and mass transport of larger molecular weight substrates and feeds that are insoluble in water. The biocatalyst would then contact a higher concentration of substrates that are insoluble or poorly-soluble in aqueous media and the reactivity would be improved. In addition, some enzymes have been shown to alter their reactivity in non-aqueous media. The development of these new microorganisms that are stable in non-aqueous media allows us to explore the potential for improved or modified reactivity of organisms in non-aqueous media.

SUMMARY OF THE PRESENT INVENTION

The present invention includes microorganisms that are resistant to non-aqueous solvents. In addition, the organisms of interest are able to grow and/or carry out various organic (e.g. hydrocarbon) transformations in non-aqueous/aqueous mixtures. Such mixtures include hydrocarbons, organic solvents, petroleum, petrochemical feeds, hydrocarbon natural resources such as crude oil, bitumen, coal and/or materials derived therefrom. In general, non-aqueous solvents can be toxic to microorganisms. In the present invention, most processes are carried out in non-aqueous/aqueous solvent ratios of at least 0.1, a level which is normally highly toxic. In the most preferred embodiment, the non-aqueous/aqueous solvent ratio is greater than 0.5.

The processes of the present invention include organic transformations such as substrate biooxidation, bioreduction, biodesulfurization, biodemetallation, biodenitrogenation, and biocleavage reactions. The non-aqueous solvent may be aromatic and/or aliphatic including hexadecane, methylnaphthalene, phenyloctane, tetralin, cyclohexane, propylbenzene or 1,2-dihydronaphthalene.

In other embodiments, the non-aqueous/aqueous mixtures include hydrocarbons, organic solvents, petroleum and petrochemical feeds such as crude oil, bitumen, coal and materials derived thereof.

The present invention also includes a gene which encodes an enzyme, hydroperoxide reductase, which renders the host microorganism resistant to many organic solvents. The invention also includes the operon which includes the mutant gene and the ahpF gene which encodes an NAD(P)H dehydrogenase. The invention also includes a plasmid vehicle and a host microorganism containing these genes.

The present invention also includes cloning the genes encoding for solvent-resistance into other organisms rendering them solvent-resistant. In addition, the invention includes placing the genes encoding for a specific organic or hydrocarbon transformation such as aromatic oxidation into the solvent-resistant microorganisms.

BRIEF DESCRIPTION OF THE DRAWINGS

FIG. 1 shows the growth of the wild type and the mutant strain in the absence of tetralin and in the presence of 50% tetralin.

FIG. 2 shows a deletion mapping of tetralin resistance locus.

FIG. 3 shows a schematic diagram for tetralin metabolism in *Escherichia coli*.

FIG. 4 shows the initial steps in the metabolism of napthalene and pyrelene by microorganisms.

DESCRIPTION OF THE PREFERRED EMBODIMENT

Most bacterial species are sensitive to organic solvents. One possible cause of the sensitivity is believed to be due to solvents partitioning into the membrane and producing a proton leak, leading to uncoupling of oxidative phosphorylation (J. Sikkema, B. Poolman, W. N. Konings, J. A. M. de Bont, 1992, J. Bacteriol, 174:2986–2992 and J. Sikkema, J. A. M. de Bont, B. Poolman, 1994, J. Biol. Chem., 269:8022–8028). Since soil microorganisms can harbor plasmids carrying genes for the catabolism of hydrocarbons, bacteria must confront organic solvents in nature. For example, the TOL plasmid allows *Pseudomonas putida* to use toluene as the sole source of carbon. Due to its toxicity, however, toluene has to be administered to *P. putida* cultures in the form of vapor or at low concentrations in the media. At the same time, mutants of both Pseudomonas and *E. coli* highly resistant to organic solvents were isolated (R. Aono, K. Aibe, A. Inoue, K. Horikoshi, 1991, Agric. Biol. Chem. 55:1935–1938 and A. Inoue, K. Horikoshi, 1989, Nature 338:264–265). Colonies of these mutants grow on plates overlaid with organic solvents. The nature of organic solvent resistance remains unknown. It is possible that mechanisms protect cells from uncouplers of oxidative phosphorylation, including multidrug resistance pumps (O. Lomovskaya, K. Lewis, 1992, Proc. Natl. Acad. Sci. USA 89:8938–8942 and V. Naroditskaya, M. J. Schlosser, M. J. Fang, N.Y., K. Lewis, 1993, Biochem. Biophys. Res. Comm. 196:803–809 and K. Lewis, 1994, Trends Biochem. Sci. 19: 119–123) and may play a role in organic solvent resistance. (K. Lewis, V. Naroditskaya, A. Ferrante, I. Fokina, 1994, Uncoupler resistance in bacteria, J. Bioenerg. Biomembr., accepted).

In the present invention, organisms are identified that are resistant to organic solvents and carry out a variety of hydrocarbon transformations including biodesulfurization, and the oxidation of aromatic and aliphatic hydrocarbons. Genes are identified and cloned which confer organic solvent resistance in *E. coli*. The mechanism of resistance involves enzymatic reduction of hydroperoxides.

OBTAINING TETRALIN-RESISTANT MUTANTS

A wild type *E. coli* K12 (strain CAG18492) carrying a transposon Tn10(tet) insertion at 81.75 min (M. Singer, T. A. Baker, G. Schnitzler, S. M. Deischel, M. Goel, W. Dove, K. F. Jaacks, A. D. Grossman, J. W. Erickson, C. A. Gross, 1989, Microbiol. Rev. 53:1–24) was tested for resistance to 1,2,3,4-tetrahydronaphthalene (tetralin). Cells from a liquid culture were streaked on an agar plate with LB medium supplemented with 0.4% glucose and 10 mM MgSO$_4$ (Medium A) and incubated at 37° C. (Aono. R., K. Aibe, A. Inoue, and K. Horikoshi 1991. Agric. Biol. Chem. 55:1935–1938). No growth was apparent indicating that *E. coli* was highly sensitive to tetralin.

In order to obtain tetralin-resistant mutants, cells were grown to late-logarithmic state in LB medium, concentrated 10-fold, and approximately $10^9$ cells were plated on a medium A plate. The agar was then overlaid with 20 mL of tetralin, and the plate was sealed and incubated at 37° C. After an overnight incubation, resistant colonies appeared on the plates. In order to verify that the resistant mutants were indeed derived from the parent strain, rather than being contaminants, the mutants were streaked on tetracycline plates. All of them appeared to be tetracycline-resistant, confirming the presence of Tn10. It was also important to learn if the resistant trait was a stable feature. To this end, the mutants were streaked on an LB plate and grown without tetralin. Then, colonies were streaked on medium A plates and overlaid with tetralin. The parent strain was included as a control. The mutants grew well under the organic solvent layer, while the wild type produced no colonies.

Growth of solvent-resistant mutants. It was important to ascertain whether the mutant cells would grow in a dispersed state in an emulsion of tetralin in aqueous solution. We found that KLE400 grew well in a 50% tetralin emulsion, with a generation time of 43 min versus 33 min in the control without tetralin. The growth of resistant mutants in a tetralin emulsion is illustrated in FIG. 1. Cells were inoculated in a 50% emulsion of tetralin in medium A and were incubated with aeration at 37° C. Samples were taken at times indicated and plated for colony counting. Note that the wild-type strain CAG18492 rapidly died off in the presence of tetralin. Interestingly, KLE400 was able to grow even in a 99% tetralin emulsion.

KLE400 was tested for resistance to a variety of other hydrocarbons using the overlay assay. The mutant was found to be resistant to cyclohexane, propylbenzene, and 1,2-dihydronaphthalene, indicating that the mutation conferred broad resistance to the strain (Table 1).

Mapping of the solvent-resistant mutation. A set of Hfr strains for rapid mapping was used to locate the chromosomal position of the organic solvent-resistant mutation as previously described (Singer, M., Baker, T. A., Schnitzler, G., Deischel, S. M., Goel, M., Dove, W., Jaacks, K. F., Grossman, A. D., Erickson, J. W. & Gross, C. A. (1989) *Microbiol. Rev.* 53, 1–24.). Each of the six strains in the set has a known origin of chromosome transfer, and a Tn10, kanamycin insertion 15–20 min. downstream of the origin. The set covers the 100-minute chromosome of *E. coli*. The KLE400 strain was mated with strains of the Hfr set for 30 minutes, after which the mating pairs were disrupted by vortexing and the progeny were selected for kanamycin and tetracycline resistance. The progeny of the matings were then screened for the loss of tetralin resistance. The resistance locus was mapped to approximately 16±5 min using this approach.

Cloning solvent resistance. DNA from strain KLE400 was isolated, digested with Sau3A1 and separated on an agarose gel as previously described. (Sambrook, J., Fritsch, E. F. & Maniatis, T. (1989) in *Molecular Cloning: A Laboratory Manual* (Cold Spring Harbor Lab., Cold Spring Harbor, N.Y.), 2nd ed.) Fragments of 4–6 kB were purified from the gel and were ligated into the plasmid vector pACYC184. The library from KLE400 was transformed into *E. coli* DH5αcells and plated on LB medium with chloramphenicol to select for transformants. Colonies from this library were then replicated onto medium A plates that were overlaid with tetralin to screen for resistant colonies. Among approximately 2,200 colonies tested, there were two resistant clones. Only one of them appeared to carry an insert in the vector DNA. This recombinant plasmid, pAF1, was reintroduced by transformation into DH5α. This DH5α(pAF1) strain was resistant, confirming that the genes conferring tetralin resistance could be cloned and introduced into another organism, and that the new recombinant organism was resistant to organic solvents including tetralin, cyclohexane, propylbenzene, and 1,2-dihydronapthalene.

Deletion mapping and the sequence of the resistance gene. A 0.9 kB EcoRV fragment and a 1.6 kB ClaI fragment were deleted from pAF1 to give pAF2 and pAF3, respectively. The restriction map of the tetralin resistant locus is illustrated in FIG. 2 for pAF1, pAF2 and pAF3.

The smallest fragment conferring resistance was 3.1 kB (pAF2). Primers to pACYC184 were used to sequence both ends of the insert. The sequence of a 286 bp portion appeared to almost perfectly match the sequence of the ahpC gene in the GenBank database. The ahpC gene is located at 14.2 min., in agreement with the position of the resistance locus obtained by genetic mapping at 16±5 min. The ahpCF operon encodes alkylhydroperoxide reductase (AHPR), an enzyme that detoxifies organic hydroperoxides and is induced by the oxidation stress response (Smillie, D. A., R. S. Hayward, T. Suzuki, N. Fujita, A. Ishihama, 1992, J. Bact. 174:3826–3827 and L. A. Tartaglia, G. Storz, M. H. Brodsky, A. Lai, and B. N. Ames, 1990, J. Biol. Chem. 265:10535–10540, and Smillie, D. A., Fujita, N., McQuay, S., Ishihama, A. & Hayward, R. S. (1993) GenBank DNA Sequence Database, accession number D13187). The ahpC protein is a small subunit (21 kDa) containing the catalytic site, and the ahpF protein is the NAD(P)H dehydrogenase.

The surprising finding of AHPR involvement suggested an unexpected hypothesis for the nature of the organic solvent toxicity and resistance, such that tetralin, cyclohexane, propylbenzene, 1,2-dihydronaphthalene are not toxic to *E. coli*, but form toxic hydroperoxides in the cell. AHPR confers resistance by reducing the hydroperoxides. The scheme for the oxidation of tetralin to tetralin hydroperoxide and of subsequent reduction of tetralin hydroperoxide to 1,2,3,4-tetrahydro-1-naphthol is depicted below and in FIG. 3.

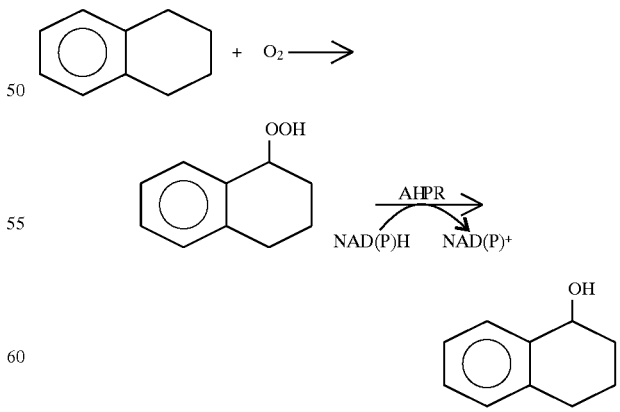

The ahpC gene from the mutant KLE400 was completely sequenced. There was a single amino acid change in the predicted gene product as compared to the predicted product of the *E. coli* ahpC gene in the database: a valine for glycine substitution at amino acid position 142 corresponding to nucleotide position 425 as indicated in SEQ. ID, NO: 1 (wild type) and SEQ. ID NO: 2 (mutant). Interestingly, not only the *E.coli* strain K12 variant W3110 but also the published *Salmonella typhimurium* ahpC sequence has a glycine residue at position 142, indicating that it is conserved. This finding suggests that a change in the catalytic subunit of alkylhydroperoxide reductase might increase the activity of the enzyme to organic hydroperoxides. The natural substrates of alkylhydroperoxide reductase are believed to be oxidation products of fatty acids. A hypothesis to account for the mutant phenotype of the enzyme is that a valine for glycine substitution increases the hydrophobicity of a catalytic site and shifts the substrate specificity of the enzyme so that it can accommodate other substrates.

Resistance properties of the ahpC* strain. The resistant mutant KLE400 as well as a strain carrying the cloned mutant genes ahpCF* and ahpC* were tested for resistance to a large number of organic solvents (Table 1). Note that the wild type *E. coli* used is also resistant to 1-methylnaphthalene.

Disc diffusion assays were used to further study resistance properties conferred by the aphC* mutation. If the mechanism of resistance was indeed based on the ability of the KLE400 strain to efficiently reduce organic hydroperoxides, then this mutant would be more resistant to the externally applied hydroperoxides as well. The disc diffusion assay was used to measure resistance of KLE400 to a number of compounds (Table 2). The test substances were applied on a disc of filter paper that was placed on a growing lawn of cells. The diffusion of the substance produced a clear zone of killing that was measured in centimeters. By this test, KLE400 had a higher resistance than the wild type to tetralin hydroperoxide, and also to cumene hydroperoxide (Table 2).

Next, the rate of the enzymatic reduction of tetralin hydroperoxide was quantified by measuring the reaction product, 1,2,3,4-tetrahydro-1-naphthol, as a function of time using capillary gas chromatography. Initial rates of 1.7±0.4 $\mu M/min/A_{600}$ for strain CAG18492 and 5.6±0.4 $\mu M/min/A_{600}$ for KLE400 were obtained. This represents more than a 3-fold increase in the rate of tetralin hydroperoxide reduction in the mutant compared to the wild type. These results indicate that KLE400 carries a mutation enhancing the activity of AHPR.

CLONING GENES FOR AROMATIC HYDROCARBON OXIDATION INTO SOLVENT-RESISTANT *E. COLI*

Bacterial catabolic pathways for the degradation of aromatic compounds generally proceed through the introduction of oxygen to the molecule to eventually form a dihydroxylated intermediate. The initial steps in the metabolism of napthalene and pyrlene by microorganisms are illustrated in FIG. 4. The latter compound is then subject to ring cleavage by one of several mechanisms. Further enzymatic reactions lead to TCA cycle intermediates. The genes coding for several of these catabolic pathways have been cloned and in many cases the nucleotide sequence of the genes has been determined. Manipulation of the aromatic oxygenation genes in *E. coli* leads to production of the desired enzymatic activity on demand, often at levels higher than that obtained with the organism from which the genes were cloned.

Clones Utilized

Two different sets of genes coding for two different catabolic pathways were utilized in the present experiments. The first set is that of the genes for polycyclic aromatic hydrocarbon degradation cloned from Pseudomonas sp. strain XPW-2. The genes have been cloned in the expression vector pTRC99A and the resulting plasmid has been designated pGJZ1403. This plasmid contains the genes coding for the production of a polycyclic aromatic hydrocarbon dioxygenase that catalyzes the addition of oxygen into the aromatic nucleus to form a cis-dihydrodiol compound. Dehydration of the cis-dihydrodiol compound by a simple chemical reaction leads to the formation of a monohydroxylated aromatic compound. The second set of genes are those for the degradation of monocyclic aromatic compounds cloned from Pseudomonas sp. strain GZ9. These genes have also been cloned into the expression vector pTRC99A and the resulting plasmid has been designated pGJZ1151. This plasmid contains the genes coding for the production of a monocyclic aromatic hydrocarbon dioxygenase that catalyzes the addition of oxygen to the aromatic nucleus to form a cis-dihydrodiol compound. Dehydration of the cis-dihydrodiol compound leads to the formation of monohydroxylated compounds. The dioxygenase coded for by pGJZ1151 is also able to oxygenate naphthalene and biphenyl. Clones are also available for the formation of dihydroxylated aromatic compounds and ring-cleaved aromatic compounds starting with monocyclic or polycyclic aromatic compounds.

Introduction of the Cloned Genes Into KLE400

The two plasmids pGJZ1151 and pGJZ1403 were isolated from the *E. coli* host strain DH5α. The purified plasmid DNA was transformed into the solvent resistant strain KLE400 by a standard calcium chloride-glycerol transformation procedure. Transformed cells were selected for resistance to ampicillin, indicating the presence of the plasmid. Colonies were then screened for the ability to produce indigo from indole, indicative of aromatic dioxygenase activity. All clones showed the ability to produce indigo, indicating that the genes for the aromatic dioxygenase were being expressed in *E. coli* KLE400 and that active dioxygenase enzyme was produced. Lysis of the cells and purification of the plasmid DNA indicated that the appropriate size plasmid was contained by the transformed strain.

Transformation of Aromatic Compounds by KLE400 Containing the Cloned Genes

The ability of *E. coli* KLE400 containing either pGJZ1151 or pGJZ1403 to produce cis-dihydrodiols from aromatic compounds was analyzed. The strains were grown in minimal medium containing glucose and ampicillin to mid log phase (optical density=0.5). The genes were then induced by the addition of IPTG to a final concentration of 1 mM. Growth of the strain under inducing conditions was continued for 1 hour when the optical density of the culture reached approximately 1.0. The cells were harvested, washed with 50 mM Na/K $PO_4$ pH 7.2 buffer, and resuspended in the same buffer to a final volume of 25 mL at an optical density of 2.0. In the case of KLE400(pGJZ1403) naphthalene was added to the cell suspension at a final concentration of 2 mg/mL. In the case of KLE400 (pGJZ1151) toluene was added in the vapor phase using a bulb suspended above the liquid medium. The cultures were monitored for the production of a cis-dihydrodiol compound by UV/Vis spectroscopy of culture supernatants. After an overnight incubation the cells were removed by centrifugation and the supernatant extracted with three equal volumes of ethylacetate. The organic fractions were pooled, dried over anhydrous sodium sulfate, and evaporated to dryness. The cis-dihydrodiol compounds were resuspended in 3 mL of methanol and analyzed by HPLC and GC-MS to verify the identity of the product using known standards. Similar experiments were conducted with 2.5 mL of tetralin added to the cell transformation mixture. In both cases, with and without tetralin, KLE400(pGJZ1151) converted toluene to cis-toluene dihydrodiol and KLE400(pGJZ1403) converted naphthalene to cis-naphthalene dihydrodiol.

Controls using E. coli without the plasmids containing the dioxygenase genes were unable to convert aromatic hydrocarbons. In addition, when E. coli that was unable to grow in tetralin or cyclohexane contained the cloned dioxygenase genes, the E. coli could convert aromatic hydrocarbons but was unable to grow in tetralin or cyclohexane.

OBTAINING XYLENE-RESISTANT MICROORGANISMS

This invention also includes the isolation, identification and characterization of microorganisms that are stable in high concentrations of xylene. In order for any bioprocess involving non-aqueous feeds, solvents or products to be viable, the biocatalysts must be stable and active in non-aqueous media. This discovery involves the identification and isolation of E. coli mutants that are resistant to high concentrations of xylene. This invention is particularly interesting because xylene has been known as a particularly toxic chemical that is thought to disrupt the cell membrane. Since many petrochemical feeds of interest contain aromatic moieties, the stability of microorganisms in aromatic solvents such as xylene is particularly important for any bioprocess involving the production of fuels and chemicals.

These mutant E. coli organisms were isolated by taking samples of the tetralin-resistant E. coli mutants described here and plating them out on agar plates that were flooded with a 30% p-xylene/70% tetralin mixture. The mutant E. coli that grew under these conditions were shown to be resistant to high concentrations of xylene. The original E. coli strains and the mutant E. coli strains that were shown to be resistant to tetralin were not resistant to xylene. Two different types of these new xylene resistant mutants were identified. One class of mutants was also resistant to antibiotics while the other class was not resistant to antibiotics. This indicates that there are two different classes of xylene-resistant mutants. It is suggested that one xylene-resistant mechanism involves altering the permeability of the cell membrane to non-aqueous compounds such as xylene. The nature of the other mechanism is unclear.

In each of these systems, the mutant E. coli organisms can be used to do various hydrocarbon transformations of interest including biodesulfurization, biodenitrogenation, biodemetallation, biocleavage reactions and the biooxidation of aromatic and aliphatic hydrocarbons. This can be achieved by placing the genes encoding for the desired biotransformation into this newly isolated solvent-resistant E. coli organism. This was demonstrated by placing the genes encoding for the oxidation of polynuclear aromatic hydrocarbons into the tetralin-resistant E. coli. Similarly, genes encoding for the oxidation of mononuclear aromatic hydrocarbons have been placed in this new tetralin-resistant organism as well. It is expected that this will improve the reactivity of the biocatalyst for the conversion of heavy hydrocarbon feeds in several ways. By improving the stability of the biocatalyst in tetralin, the biocatalyst will remain active longer. It is also expected that use of the tetralin-resistant mutant will improve contacting between the hydrocarbon substrate and the biocatalyst thereby enhancing the reactivity.

The isolation and characterization of these new solvent-resistant mutants will be important for developing a viable bioprocess for the transformation and upgrading of hydrocarbon feeds. These organisms can be utilized to develop solvent-resistant organisms that do various organic transformations including biodesulfurization, biodenitrogenation, biodemetallation, biocleavage reactions and the oxidation of aromatic and aliphatic hydrocarbons. Use of these solvent-resistant organisms will result in enhanced reactivity and stability of the biocatalysts.

OTHER SOLVENT-RESISTANT ORGANISMS THAT PERFORM HYDROCARBON TRANSFORMATIONS

This invention provides solvent-resistant organisms that are capable of doing a variety of organic (e.g., hydrocarbon) transformations in non-aqueous media. The type of transformations considered important for the purpose of this invention include but are not restricted to substrate biooxidation or bioreduction, biodesulfurization, biodenitrogenation, biodemetallation, and biocleavage reactions. These biotransformations would include conversions of the following non-aqueous materials including hydrocarbons, petroleum, chemical, and/or pharmaceutical feeds, natural resources including crude oil, bitumen, coal and/or materials derived from these resources.

A representative of another group of microorganisms that have been identified as solvent-resistant includes a Rhodococcus species designated strain D-12, that performs organic transformations. This organism was isolated from refinery soils and was identified as a gram positive organism that is capable of oxidizing aromatic and aliphatic hydrocarbons such as hexadecane, dibenzothiophene, phenanthrene, and anthracene. This organism was plated on Trypticase Soy Agar in glass petri dishes. The agar was overlaid with approximately 20 mL of organic solvent and incubated at 25° C. After several days, growth of the organism was clearly visible. The organism was found to be resistant to phenyloctane, hexadecane, methylnaphthalene, and a hydrofined light cat cycle oil (LCCO). LCCO is a distillate cut from a catalytic cracking unit and has a boiling point range between 350° F.–700° F. Other solvents that were tested are listed in Table 3.

Another organism identified as solvent resistant includes the biodesulfurization organism, ECRD-1, deposited in the ATCC culture collection as Arthrobacter species ATCC 55309. This microorganism was obtained from marine soil and has been previously shown to selectively remove sulfur from a variety of organosulfur containing compounds including dibenzothiophene, DBT. ECRD-1 was plated on Trypticase Soy Agar in glass petri dishes. The agar was overlaid with approximately 20 mL of organic solvent and incubated at 25° C. After several days, growth of the organism was clearly visible. The organism was found to be resistant to phenyloctane, hexadecane, methylnaphthalene, and a hydrofined light cat cycle oil (LCCO). Other solvents that were tested are listed in Table 3.

TABLE 1

GROWTH OF E. COLI STRAINS ON SOLID MEDIA OVERLAYED WITH ORGANIC SOLVENT

| SOLVENT | wild type (CAG 18492) | mutant (KLE 400) | clone 1 (ahpCF) (DH5α(PAF1)) | clone 2 (ahpC) (DH5α(PAF22)) |
|---|---|---|---|---|
| hexane | + | + | + | + |
| pentane | − | − | − | − |
| cyclooctane | + | + | + | + |
| cyclohexane | − | + | + | + |
| methylcyclohexane | + | + | + | + |
| cyclopentane | − | − | − | − |
| cyclohexene | − | − | − | − |
| cyclohexanol | − | − | − | − |
| toluene | − | − | − | − |
| ethylbenzene | − | − | − | − |
| propylbenzene | − | + | + | + |
| p-xylene | − | − | − | − |
| diphenylether | + | + | + | + |
| 1-methylnaphthalene | + | + | + | + |
| 1,2-dihydronaphthalene | − | + | + | − |
| tetralin | − | + | + | + |
| decalin | + | + | + | + |
| 1-methylnaphthalene + anthracene (1% wt/vol) | + | + | + | + |
| + dibenzothiophene (1% wt/vol) | + | + | + | + |
| + carbazole (1% wt/vol) | + | + | + | + |
| + quinoline (1% wt/vol) | + | + | + | + |
| carbon tetrachloride | − | − | − | − |

Footnotes to Table 1

[a]Resistance to organic solvents was tested using the solvent overlay plate technique. The signs refer to the ability (+) or inability (−) of the cells to grow when overlaid with organic solvent. CAG18492 and KLE400 are wild-type and mutant strains, respectively.

TABLE 2

Resistance of wild-type and mutant E. coli strains to various peroxides.[a]

| | Diameter of the zone of growth inhibition (cm) | | |
|---|---|---|---|
| Strain | tetralin hydroperoxide | cumene hydroperoxide | hydrogen peroxide |
| CAG18492[b] | 1.6 ± 0.1 | 2.0 ± 0.1 | 2.0 ± 0.1 |
| KLE400[c] | 1.1 ± 0.2 | 1.4 ± 0.1 | 1.9 ± 0.2 |

Footnotes to Table 2

[a]Resistance was tested using antimicrobial disk assays in which filter paper disks containing the test compound were placed on a lawn of growing bacteria. The hydroperoxides diffused from the disk forming a concentration gradient. Cells with higher resistance were able to grow closer to the disks, thus affording smaller diameters of the zone of growth inhibition. All experiments were conducted in triplicate, and the mean values and standard deviations are reported.

[b]Wild-type strain.

[c]Mutant strain.

TABLE 3

Solvent-resistance of organisms that carry out organic transformations.

| SOLVENT | Rhodococcus D-12[a] | Biodesulfurization D-1[b] |
|---|---|---|
| Cyclohexane | NT[c] | − |
| Hexadecane | + | + |
| Hexane | NT | − |
| LCCO | + | + |
| Methylene chloride | NT | − |
| Methylnaphthalene | + | + |
| Phenyloctane | + | + |
| Tetralin | − | − |
| Toluene | − | − |

[a]Rhodococcus organism, D-12, capable of oxidizing aromatic and aliphatic hydrocarbons.

[b]Biodesulfurization organism, ECRD-1, capable of selectively removing sulfur from a variety of organosulfur containing compounds including DBT.

[c]NT indicates not tested.

We claim:

1. An isolated gene having the nucleotide base sequence listed in SEQ ID NO. 2.

2. An isolated operon comprising the gene of claim 1 and further comprising a gene ahpF encoding for NAD(P)H dehydrogenase wherein said ahpF gene is from the *Escherichia coli* genome.

3. A plasmid comprising the operon of claim 2.

4. A recombinant microorganism including the gene of claim 1.

5. A recombinant microorganism including the operon of claim 2.

6. A recombinant microorganism which is transformed with a gene having SEQ ID NO: 2 wherein said gene encodes a hydroperoxide reductase enzyme that renders said microorganism resistant to non-aqueous solvents.

7. The recombinant microorganism of claim 6 which includes a gene having the nucleotide base sequence listed in SEQ ID No. 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
ATGTCCTTGA    TTAACACCAA    AATTAAACCT    TTTAAAAACC    AGGCATTCAA    50
AAACGGCGAA    TTCATCGAAA    TCACCGAAAA    AGATACCGAA    GGCCGCTGGA    100
GCGTCTTCTT    CTTCTACCCG    GCTGACTTTA    CTTTCGTATG    CCCGACCGAA    150
CTGGGTGACG    TTGCTGACCA    CTACGAAGAA    CTGCAGAAAC    TGGGCGTAGA    200
CGTATACGCA    GTATCTACCG    ATACTCACTT    CACCCACAAA    GCATGGCACA    250
GCAGCTCTGA    AACCATCGCT    AAAATCAAAT    ATGCGATGAT    CGGCGACCCG    300
ACTGGCGCCC    TGACCCGTAA    CTTCGACAAC    ATGCGRGAAG    ATGAAGGTCT    350
GGCTGACCGT    GCGACCTTCG    TTGTTGACCC    GCAGGGTATC    ATCCAGGCAA    400
TCGAAGTTAC    CGCTGAAGGC    ATTGGCCGTG    ACGCGTCTGA    CCTGCTGCGT    450
AAAATCAAAG    CAGCACAGTA    CGTAGCTTCT    CACCCAGGTG    AAGTTTGCCC    500
GGCTAAATGG    AAAGAAGTTG    AAGCAACTCT    GGCTCCGTCT    CTGGACCTGG    550
TTGGTAAAAT    CTAA                                                  564
```

( 2 ) INFORMATION FOR SEQ ID NO:2:

( i ) SEQUENCE CHARACTERISTICS:
        ( A ) LENGTH: 564 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
ATGTCCTTGA    TTAACACCAA    AATTAAACCT    TTTAAAAACC    AGGCATTCAA    50
AAACGGCGAA    TTCATCGAAA    TCACCGAAAA    AGATACCGAA    GGCCGCTGGA    100
GCGTCTTCTT    CTTCTACCCG    GCTGACTTTA    CTTTCGTATG    CCCGACCGAA    150
CTGGGTGACG    TTGCTGACCA    CTACGAAGAA    CTGCAGAAAC    TGGGCGTAGA    200
CGTATACGCA    GTATCTACCG    ATACTCACTT    CACCCACAAA    GCATGGCACA    250
GCAGCTCTGA    AACCATCGCT    AAAATCAAAT    ATGCGATGAT    CGGCGACCCG    300
ACTGGCGCCC    TGACCCGTAA    CTTCGACAAC    ATGCGRGAAG    ATGAAGGTCT    350
GGCTGACCGT    GCGACCTTCG    TTGTTGACCC    GCAGGGTATC    ATCCAGGCAA    400
TCGAAGTTAC    CGCTGAAGGC    ATTGTCCGTG    ACGCGTCTGA    CCTGCTGCGT    450
AAAATCAAAG    CAGCACAGTA    CGTAGCTTCT    CACCCAGGTG    AAGTTTGCCC    500
GGCTAAATGG    AAAGAAGTTG    AAGCAACTCT    GGCTCCGTCT    CTGGACCTGG    550
TTGGTAAAAT    CTAA                                                  564
```